US008968275B2

(12) United States Patent
Piskun et al.

(10) Patent No.: US 8,968,275 B2
(45) Date of Patent: *Mar. 3, 2015

(54) APPARATUS AND METHOD FOR EFFECTING AT LEAST ONE ANATOMICAL STRUCTURE

(75) Inventors: Gregory Piskun, Morganville, NJ (US); Patrick Gutelius, Monroe, CT (US); Oleg Shikhman, Trumbull, CT (US)

(73) Assignee: Covidien LP, Mansfield, MA (US)

(*) Notice: Subject to any disclaimer, the term of this patent is extended or adjusted under 35 U.S.C. 154(b) by 147 days.

This patent is subject to a terminal disclaimer.

(21) Appl. No.: 13/094,173

(22) Filed: Apr. 26, 2011

(65) Prior Publication Data

US 2011/0288538 A1    Nov. 24, 2011

Related U.S. Application Data

(60) Provisional application No. 61/328,005, filed on Apr. 26, 2010.

(51) Int. Cl.
| *A61B 17/00* | (2006.01) |
| *A61B 1/00* | (2006.01) |
| *A61M 29/00* | (2006.01) |
| *A61B 17/3205* | (2006.01) |
| *A61B 17/22* | (2006.01) |
| *A61B 17/34* | (2006.01) |

(Continued)

(52) U.S. Cl.
CPC ....... *A61B 17/3205* (2013.01); *A61B 17/22031* (2013.01); *A61B 17/3421* (2013.01);
(Continued)

(58) Field of Classification Search
CPC ............ A61B 1/06; A61B 1/31; A61B 17/22; A61B 17/3205; A61B 18/14; A61B 2017/3452; A61B 2018/005; A61B 2019/302–2019/305

USPC ................ 600/129; 606/1, 110, 112, 197
See application file for complete search history.

(56) References Cited

U.S. PATENT DOCUMENTS

| 457,787 A | 8/1891 | Leisenring |
| 2,482,971 A | 9/1949 | Golson |

(Continued)

FOREIGN PATENT DOCUMENTS

| EP | 0736285 | 10/1996 |
| GB | 2365340 | 2/2002 |

(Continued)

OTHER PUBLICATIONS

PCT/US2011/033875—International Search Report and Written Opinion.

(Continued)

*Primary Examiner* — Lynsey Crandall
*Assistant Examiner* — Nathan J Jenness

(57) ABSTRACT

Exemplary embodiments of apparatus and method for effecting at least one anatomical structure of a body can be provided. For example, at least one first arrangement can be provided which is structured to be at least partially inserted into the body and including an opening. In addition, at least one second arrangement can be provided which configured to increase and/or decrease a size of the opening by a motion thereof in a first direction. Further, at least one third arrangement can be provided which can be coupled to the second arrangement(s), and configured to move at least in a second direction which is at least approximately parallel to the second direction. In particular, when the anatomical structure(s) is/are provided or inserted in the opening and is pressed on by the second arrangement(s), a first motion of the second arrangement(s) toward the anatomical structure(s) in the first direction is reduced and/or terminated while a second motion of the third arrangement(s) in the second direction either (i) remains at least approximately the same, and/or (ii) is reduced to a lesser extent than that of the first motion.

15 Claims, 13 Drawing Sheets

(51) Int. Cl.
*A61B 1/06* (2006.01)
*A61B 17/02* (2006.01)
*A61B 17/12* (2006.01)
*A61B 18/18* (2006.01)
*A61B 19/00* (2006.01)

(52) U.S. Cl.
CPC ...... *A61B 1/06* (2013.01); *A61B 17/02* (2013.01); *A61B 17/12013* (2013.01); *A61B 18/18* (2013.01); *A61B 19/5202* (2013.01); *A61B 2017/3452* (2013.01); *A61B 2019/302* (2013.01)
USPC ............... 606/1; 600/129; 606/112; 606/197; 606/207

(56) References Cited

U.S. PATENT DOCUMENTS

| | | | |
|---|---|---|---|
| 3,382,873 A | 5/1968 | Banich et al. | |
| 3,760,810 A | 9/1973 | Van Hoorn | |
| 4,257,419 A | 3/1981 | Goltner et al. | |
| 5,318,589 A * | 6/1994 | Lichtman | 606/205 |
| 5,402,772 A | 4/1995 | Moll et al. | |
| 5,411,508 A | 5/1995 | Bessler et al. | |
| 5,443,472 A * | 8/1995 | Li | 606/114 |
| 5,570,692 A | 11/1996 | Morinaga | |
| 5,655,698 A | 8/1997 | Yoon | |
| 5,665,062 A | 9/1997 | Houser | |
| 5,716,321 A | 2/1998 | Kerin et al. | |
| 5,873,815 A | 2/1999 | Kerin et al. | |
| 5,876,369 A | 3/1999 | Houser | |
| 5,935,056 A | 8/1999 | Kering et al. | |
| 5,947,983 A | 9/1999 | Solar et al. | |
| 5,968,033 A * | 10/1999 | Fuller et al. | 606/9 |
| 6,019,733 A | 2/2000 | Farascioni | |
| 6,032,673 A * | 3/2000 | Savage et al. | 128/898 |
| 6,102,271 A | 8/2000 | Longo et al. | |
| 6,119,913 A | 9/2000 | Adams et al. | |
| 6,126,594 A | 10/2000 | Bayer | |
| 6,142,931 A | 11/2000 | Kaji | |
| 6,142,933 A | 11/2000 | Longo et al. | |
| 6,179,832 B1 | 1/2001 | Jones et al. | |
| 6,196,966 B1 | 3/2001 | Kerin et al. | |
| 6,214,024 B1 | 4/2001 | Houser | |
| 6,264,086 B1 | 7/2001 | McGuckin, Jr. | |
| 6,277,065 B1 | 8/2001 | Donofrio | |
| 6,277,066 B1 | 8/2001 | Irwin | |
| 6,302,311 B1 | 10/2001 | Adams et al. | |
| 6,343,731 B1 | 2/2002 | Adams et al. | |
| 6,398,795 B1 | 6/2002 | McAlister et al. | |
| 6,428,473 B1 | 8/2002 | Leonard et al. | |
| 6,478,210 B2 | 11/2002 | Adams et al. | |
| 6,494,881 B1 | 12/2002 | Bales et al. | |
| 6,540,761 B2 | 4/2003 | Houser | |
| 6,575,978 B2 | 6/2003 | Peterson et al. | |
| 6,595,917 B2 | 7/2003 | Nieto | |
| 6,616,603 B1 | 9/2003 | Fontana | |
| 6,695,198 B2 | 2/2004 | Adams et al. | |
| 6,716,222 B2 | 4/2004 | McAlister et al. | |
| 6,805,273 B2 | 10/2004 | Bilotti et al. | |
| 6,808,491 B2 | 10/2004 | Kortenbach et al. | |
| 6,840,423 B2 | 1/2005 | Adams et al. | |
| 6,866,178 B2 | 3/2005 | Adams et al. | |
| 6,872,204 B2 | 3/2005 | Houser | |
| 6,874,669 B2 | 4/2005 | Adams et al. | |
| 6,923,806 B2 | 8/2005 | Hooven et al. | |
| 6,938,814 B2 | 9/2005 | Sharma et al. | |
| 6,979,290 B2 | 12/2005 | Mourlas et al. | |
| 7,014,646 B2 | 3/2006 | Adams | |
| 7,029,438 B2 | 4/2006 | Morin et al. | |
| 7,059,331 B2 | 6/2006 | Adams et al. | |
| 7,118,528 B1 | 10/2006 | Piskun | |
| 7,169,115 B2 | 1/2007 | Nobis et al. | |
| 7,334,718 B2 | 2/2008 | McAlister et al. | |
| 7,452,329 B2 | 11/2008 | Bastia et al. | |
| 7,534,204 B2 | 5/2009 | Starksen et al. | |
| 7,546,939 B2 | 6/2009 | Adams et al. | |
| 7,717,861 B2 * | 5/2010 | Weikel et al. | 600/566 |
| 7,882,995 B2 | 2/2011 | McAlister et al. | |
| 7,972,299 B2 | 7/2011 | Carter et al. | |
| 8,002,795 B2 * | 8/2011 | Beetel | 606/219 |
| 8,016,748 B2 | 9/2011 | Mourlas et al. | |
| 8,100,822 B2 | 1/2012 | Piskun et al. | |
| 2002/0111639 A1 | 8/2002 | Armstrong | |
| 2002/0173786 A1 | 11/2002 | Kortenbach et al. | |
| 2004/0002706 A1 | 1/2004 | Houser | |
| 2004/0033202 A1 | 2/2004 | Cooper et al. | |
| 2004/0158263 A1 | 8/2004 | McAlister et al. | |
| 2005/0119523 A1 | 6/2005 | Starksen et al. | |
| 2005/0277975 A1 | 12/2005 | Saadat et al. | |
| 2006/0049231 A1 | 3/2006 | Leiboff et al. | |
| 2006/0191975 A1 | 8/2006 | Adams et al. | |
| 2006/0200040 A1 * | 9/2006 | Weikel et al. | 600/566 |
| 2006/0264706 A1 | 11/2006 | Piskun | |
| 2007/0255207 A1 | 11/2007 | Hangai et al. | |
| 2008/0083813 A1 * | 4/2008 | Zemlok et al. | 227/181.1 |
| 2008/0103498 A1 * | 5/2008 | West et al. | 606/41 |
| 2008/0132835 A1 | 6/2008 | Nagamatsu et al. | |
| 2008/0262511 A1 | 10/2008 | Delaney | |
| 2008/0277448 A1 * | 11/2008 | Roby et al. | 227/175.1 |
| 2009/0025910 A1 | 1/2009 | Hoffman et al. | |
| 2009/0030369 A1 | 1/2009 | Nagamatsu et al. | |
| 2009/0182332 A1 * | 7/2009 | Long et al. | 606/51 |
| 2009/0182350 A1 * | 7/2009 | McGown | 606/140 |
| 2009/0187074 A1 | 7/2009 | Saadat et al. | |
| 2009/0259110 A1 | 10/2009 | Bastia et al. | |
| 2009/0318940 A1 | 12/2009 | Piskun et al. | |
| 2010/0010296 A1 | 1/2010 | Piskun et al. | |
| 2010/0010297 A1 | 1/2010 | Piskun et al. | |
| 2010/0023023 A1 * | 1/2010 | Popovic et al. | 606/142 |
| 2010/0056870 A1 | 3/2010 | Piskun et al. | |
| 2011/0224494 A1 | 9/2011 | Piskun et al. | |
| 2012/0059394 A1 | 3/2012 | Brenner et al. | |
| 2013/0053833 A1 * | 2/2013 | Doyle | 606/1 |

FOREIGN PATENT DOCUMENTS

| | | |
|---|---|---|
| JP | H01272139 A | 10/1989 |
| JP | 2006288431 A | 10/2006 |
| WO | WO 97/13451 | 4/1997 |
| WO | WO 2004/004555 | 1/2004 |
| WO | WO 2007/017854 | 2/2007 |
| WO | WO 2007/019321 | 2/2007 |
| WO | WO 2007/032776 | 3/2007 |
| WO | 2010041280 A1 | 4/2010 |
| WO | WO 2011/041578 | 4/2011 |
| WO | WO 2011/084616 | 7/2011 |

OTHER PUBLICATIONS

PCT/US2006/030464 International Search Report (Jun. 20, 2007).
PCT/US2006/030464 International Preliminary Report on Patentability (Feb. 5, 2008).
PCT/US2010/060802 International Search Report (Nov. 17, 2011).
PCT/US2010/060802 International Preliminary Report on Patentability (Jun. 19, 2012).
Notice of Reasons for Rejection for Japan Appl. No. 2008-525229 (Aug. 10, 2011).
PCT/US2010/050955 International Search Report (Jun. 23, 2011).
PCT/US06/30464 Written Opinion dated Jun. 20, 2007 and International Search Report.
European Search Report dated May 3, 2011 for European Patent Application No. 06789411.3.
Chinese Appl. No. 200680028706.2 English text of First Office Action (Jun. 20, 2007), Second Office Action (Feb. 5, 2010) and Third Office Action (Nov. 4, 2010).
Japanese Office Action dated Nov. 27, 2014 issued in Japanese Appln. No. 2013-508145.

* cited by examiner

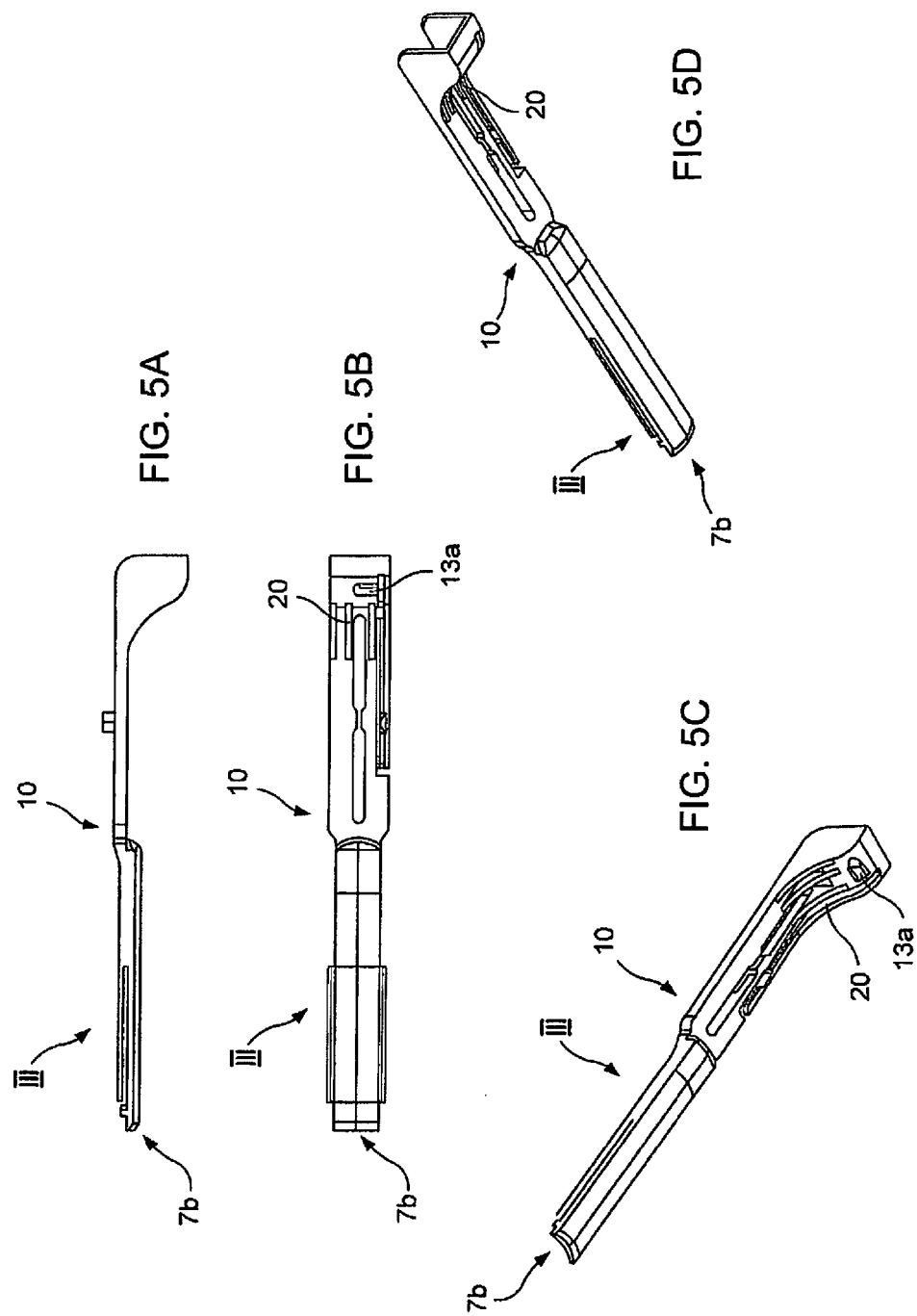

APPARATUS AND METHOD FOR EFFECTING AT LEAST ONE ANATOMICAL STRUCTURE

CROSS-REFERENCE TO RELATED APPLICATION

This application claims priority from U.S. Patent Provisional Application Ser. No. 61/328,005 filed Apr. 26, 2010, which is herein incorporated by reference in its entirety.

FIELD OF THE DISCLOSURE

The present disclosure relates to an apparatus and method for effecting at least one anatomical structure, and more particularly to exemplary embodiments of the apparatus and method to effectuate a surgical treatment of tissue masses located inside the human body, e.g., in the hollow internal organs such as the colon. The exemplary apparatus and methods can be suitable for, e.g., a treatment of hemorrhoids, as well as other conditions. The exemplary apparatus and method can be implemented to, e.g., compress a hemorrhoid or/and reduce its blood supply with a clamping instrument, while preventing a cutting of the hemorrhoid or its blood vessels with such exemplary instrument.

BACKGROUND INFORMATION

There are a variety of abnormal conditions in the body which can be related to the wall(s) of hollow organs. Colonic polyps and tumors, endothelial vascular lesions, diverticuli, and symptomatic internal hemorrhoids are some of the examples of these abnormal conditions. A treatment to such abnormal conditions from inside a hollow organ cavity or a lumen (so-called intra-luminal or endolumenal approach) may be beneficial to the patient since a surgical access trauma is reduced or eliminated.

One common condition that can be easily treated with the endoluminal approach is a symptomatic internal hemorrhoids condition. Internal hemorrhoids are conventionally treated using a variety of interventional and non-interventional endoluminal methods. An immediate proximity of internal hemorrhoids to the external orifice allows for a relatively easy access thereto. Several technologies for treating the internal hemorrhoids are currently available, but are fairly complex and/or frequently have less than acceptable clinical outcomes and/or high costs associated therewith.

Hemorrhoidal disease is a very common condition that can occur in more than half of the population by the age of 50. Currently, over 10 million people suffer symptoms from hemorrhoids in the United States, and one million new cases of symptomatic hemorrhoids are diagnosed annually. Approximately 10-20 percent of such cases may need a surgical removal of the hemorrhoid, which is associated with significant postoperative morbidity and high cost to the individuals and society.

The term "hemorrhoid" is generally used to refer to the disturbing perianal symptoms related to vascular complexes in the lower rectum and anus. This is usually associated with enlargement of this naturally occurring vascular tissue, which is responsible for its subsequent bleeding, prolapsing, thrombosis, itching, burning, etc. Repetitive straining due to constipation appears to be a leading factor in forming and progressing of hemorrhoids. The chances of having symptomatic hemorrhoids increase with age, pregnancy, obesity, sedimentary life, heavy lifting and genetic predisposition.

Various treatments can be tailored to the type and severity of the specific hemorrhoids. A pharmacological treatment, which is aimed at the regulation of defecation and symptomatic relief, may be less beneficial as likely having only a temporary and frequently incomplete effect. Current interventional, non-excisional, therapies are designed to obliterate blood supply to part of or to the entire hemorrhoid (e.g., rubber band ligation, infrared coagulation, injection sclerotherapy, ultrasound guided hemorrhoidal artery ligation, etc.). These treatments have modest, inconsistent clinical success with a frequent recurrence rate.

Rubber band ligation is one popular treatment method of hemorrhoids. In the rubber band ligation, some hemorrhoidal tissue is pulled into the ligator, and a rubber band is placed around the base of the pulled tissue. This causes a strangulation of the blood supply to a portion of the internal hemorrhoid and its overlying rectal mucosa. An ischemic necrosis and autoamputation of the hemorrhoid can generally follow in a few days, leaving an open rectal wound, which heals over several days. Severe and possibly debilitating postoperative pain is rare, but significant anal discomfort and tenesmus (a painfully urgent but ineffectual sensation or attempt to defecate) are frequent. Recurrences after the rubber band ligation are also frequent. In addition, since such treatment leaves the patient with an open wound in the anus for several days, the rubber band ligation may be rendered unsuitable for HIV-positive patients, and may require a demanding preparation for patients with bleeding disorders.

Sclerotherapy is another method for treatment of small internal hemorrhoids. A sclerosing agent is injected via a needle into and around the internal hemorrhoid. The rates of complications and recurrence of sclerotherapy can be high.

An ultrasound guided hemorrhoidal artery ligation involves manual suturing of the rectal tissues containing the hemorrhoial artery. The artery can be located by ultrasound radiation with an appropriate ultrasound arrangement. A resulting regression of the corresponding internal hemorrhoid would be expected. Since the suture-ligation can be performed above the internal hemorrhoid in the pain-insensitive zone, the procedure should be painless. However, such technique is demanding, and is highly dependent on the operator's experience and dexterity. Inexperience or lack of skill of the operator is responsible for both "missing" the hemorrhoidal artery and inadvertent rectal and vascular injuries. Hemorrhoidal artery injuries with resulting severe bleeding, rectal wall injury, etc. have been reported, and the recurrences are frequent.

The treatment of internal hemorrhoids with infrared coagulation can involve a blind heat coagulation of the branches of superior hemorrhoidal artery. Theoretically, when the branches of superior hemorrhoidal artery are successfully targeted, it can cause a subsequent regression of the corresponding internal hemorrhoid. However, since the exact location of the artery is not known, there is no guarantee that the infrared coagulation pulses reach the vessels and hence have any effect on hemorrhoids. Multiple treatments in a time span of several months are currently recommended by the distributor and treating doctors. The proper application of the infrared probe can be difficult with larger hemorrhoids due to obscurity of the interface between the probe and mucosa. Recurrences and ineffective treatment can be frequent.

Traditional surgical excision of hemorrhoids can be an effective but often a debilitating form of treatment. The hemorrhoidal tissue can be removed in longitudinal (parallel to main rectal axis) direction. Surgical excision of hemorrhoids may require the use of an anesthesia, and can cause a severe postoperative pain to the patient for several weeks along with a significant loss of work time therefor. Such technique is also dependent on the technical skill of the operator.

Another procedure, i.e., a Procedure for Prolapse and Hemorrhoids (PPH) can be used which involves circumferential excision of the rectal mucosa and submucosal layer proximal to the internal hemorrhoids using a circular stapler. As a result, a superior hemorrhoidal blood supply can be interrupted, while the hemorrhoidal tissue itself is left to ischemically regress. Since the excision is performed above the dentate line, a decreased postoperative pain and faster recovery (when compared to traditional hemorrhoidectomy) would likely occur. The internal hemorrhoids can consequently shrink within four to six weeks after such procedure. This PPH technique requires the implementation by highly skilled operators, as well as a significant learning curve, a general or regional anesthesia, and an expensive instrumental set-up. In addition, the use of PPH creates a substantial circumferential rectal trauma, which is likely excessive in the majority of cases when only 1 or 2 hemorrhoids are enlarged. A substantial circumferential injury of the anal canal and subsequent scarring can cause a rectal stricture (narrowing), which is debilitating and difficult to treat in patients. Serious complications during and after PPH have been previously reported.

Thus, there are several less invasive procedures than conventional surgery methods for the treatment of symptomatic internal hemorrhoids. However, such methods do not have the desired combination of simplicity, effectiveness and being substantially painless, minimally invasive, and inexpensive.

Accordingly, there is a need to provide a device and method which overcome at least some of the deficiencies with the previous devices and methods.

SUMMARY OF EXEMPLARY EMBODIMENTS OF THE DISCLOSURE

At least some of the objects of the present invention are to provide exemplary devices and methods to overcome at least some of the deficiencies indicated hereinabove. For example, the exemplary embodiment of the method and device may be provided which can be useful in the treatment of hemorrhoids and/or associated tissues, and can facilitate a less traumatic experience than the conventional methods and devices for the treatment of hemorrhoids. The exemplary device and method can also be utilized for treatment of other pathologies in locations remote from body openings.

With one exemplary embodiment of the method and device of the present disclosure, it is possible to effectuate an approximately constant tissue compression by a clamp arrangement, which is at least partially independent of the clamp-actuating force applied by a user to the associated handle of the exemplary device. In the exemplary embodiments described below in this Summary Section, the first component, first part and first arrangement are used interchangeably, and designated by reference numeral I in the drawings. The second component, second part and second arrangement are used interchangeably, and designated by reference numeral II in the drawings. The third component, third part and third arrangement are used interchangeably, and designated by reference numeral III in the drawings. The first spring in exemplary embodiments is designated by reference numeral 12 and the second spring is designated by reference numeral 13. The first closure member in exemplary embodiments corresponds to the first closure member 9 of part II and the second closure member in exemplary embodiments corresponds to second closure member 10 of part III.

According to one exemplary embodiment of the present disclosure, a surgical instrument can be provided which comprises an insertable arrangement having a window 6, and a closure member 10 movably connected to the insertable arrangement for alternately covering and uncovering the window, and applying pressure to or clamping any material provided within the window. The insertable arrangement can have a first (e.g., clamping) surface 7a along an edge of the window 6, and the closure member 10 can have a second (e.g., clamping) surface 7b situated opposite to the first surface to be able to selectively cover and uncover the window so as to apply a force to or clamp any tissue or object provided within the window. The exemplary instrument also includes a tissue effecting component coupled to the insertable arrangement and/or the closure member for acting on tissues gripped or clamped between the first surface 7a and the second surface 7b. The exemplary instruments also have a further arrangement which is configured to propel the second surface 7b toward the first surface 7a so as to apply pressure to or clamp any object or tissue provided in the window, and also to prevent further pressure or clamping to be applied to the object or tissue if the pressure and/or clamping thereon exceeds a particular amount of pressure.

According to a particular exemplary embodiment of the present disclosure, the instrument can have a second closure member 10 which includes the second clamping surface 7b and a first closure member 9 which is connected to a second handle grip 8. The second handle grip 8 can be part of a second arrangement II. The first and second closure members can slide in relation to each other, and are connected to one another via a spring, referred to herein as the second spring such as spring 13.

In accordance with another embodiment of the present disclosure, the device has at least two springs. A first spring 12 is affixed to a first handle grip 5 at one end and to the first closure member 9 at another end thereof at their fixation points. The first handle grip is part of a first arrangement I. A second spring 13 is affixed to the first closure member 9 at one end, and to the second closure member 10 at another end thereof at their respective fixation points. For example, according to one exemplary embodiment of the present disclosure, the springs 12, 13 can stretch between the fixation points during the window closure when the grip handles of the first and second parts (arrangements) I, II are moved toward one another. The second spring 13 provides an ability to effectuate an approximately constant tissue compression function, and avoid an unwanted excessive compression of the tissue. Each of the springs (e.g., the first spring) can facilitate a return of the closure member to its non-deployed (open) position so as to maintain the window 6 open for another insertion of the tissue or object therein.

In an exemplary operation, when a squeezing force is applied to the handle, e.g., for the purpose of compressing the tissue between the first and second clamping surfaces 7a, 7b, a second handle grip of the second component II moves towards a first handle grip of the first component I (proximal in relation to the insertion tip of the device) located distal of the second handle grip. In one exemplary embodiment, this causes the first closure member 9 to move towards the insertion tip of the device, and the second (e.g., clamping) surface 7b of the second closure member 10 moves towards the clamping surface 7a of the first component I. As the first closure member 9 moves forward toward the clamping surface 7a of the first component, the first and second springs 12, 13 are pulled in a general direction of the window 6, and are stretched.

The first spring 12 facilitates gliding of the first closure member 9 during the closure and helps return the closure member to its non-deployed (open) position after the handle is released.

The second proximal spring 13 provides the constant tissue compression function during closure and facilitates returning of the second closure member 10 to its non-deployed position after the handle is released.

When the first closure member 9 is actuated by squeezing the handle of the device and hence the second handle grip and the associated first closure member 9 move forward, the second proximal spring 13 (which is connected between first and second closure members) pulls and moves forward the second closure member 10. If the second closure member 10 doesn't meet an obstacle in the window, for example, a protruding tissue, the second clamping surface 7b of the second closure member meets the first clamping surface 7a of the first component without substantially stretching the spring 13. The device's parts are dimensioned so that when the first and second handle grips meet, the opposing first and second clamping surfaces 7a, 7b touch each other and the window closes.

If the second closure member 10 meets an obstacle in the window, for example, a protruding tissue, the second closure member 10 (and second clamping surface 7b) stops, while the first closure member 9 continues its forward movement and slides over the second closure member 10. As a result, the second spring 13 stretches and an additional (after movement of the second closure member is stopped by the tissue) squeezing force of the handle by an operator translates into forward movement of the first closure member 9 of the second component II and stretching of the second proximal spring 13. Consequently, only constant compression to the tissue is delivered as designed by the strength of the second spring 13 and the compressing tissue properties, regardless of the additional force used by an operator.

When the handle is released, the first spring 12 pulls back on first closure member 9 and its associated second handle grip and brings it back to its non-deployed (open) position.

As the first closure member 9 and its associated second handle grip is returning to its open position, the first closure member 9 pulls back on the second closure member 10 and returns it to its non-deployed (open) position. As a result, the window 6 is opened and the tissue is released.

In addition, according to one exemplary embodiment of the present disclosure, it is possible to provide a device which can be an endoluminal intervention assembly that includes an accessory system for the delivery and support (e.g., optically and/or mechanically) of instrumentation to surgical sites remote from the body openings.

In accordance with yet another exemplary embodiment of the present disclosure, apparatus and method for effecting at least one anatomical structure of a body can be provided, including at least one first arrangement I which is structured to be at least partially inserted into the body and including an opening. In addition, at least one third arrangement III can be provided which is configured to increase and/or decrease a size of the opening by a motion thereof in a first direction e.g., a distal direction. Further, at least one second arrangement II can be provided which can be coupled to the third arrangement(s) III, and configured to move at least in a distal direction which is at least approximately parallel to the first direction. In particular, when the anatomical structure(s) is/are provided or inserted in the opening and is pressed on by the third arrangement(s) III, a first motion of the third arrangement(s) III toward the anatomical structure(s) in the first direction is reduced and/or terminated while a second motion of the second arrangement(s) II in the second direction either (i) remains at least approximately the same, and/or (ii) is reduced to a lesser extent than that of the first motion.

In addition, at least one tension-setting arrangement can be provided which couples the third and second arrangements III, II to one another. The tension-setting arrangement(s) can include at least one spring 13, and when the anatomical structure is pressed by the third arrangement(s), a tension of the at least one spring 13 can be increased which causes the third arrangement(s) III to at least reduce the first motion in the first direction while facilitating the second motion of the second arrangement(s) II to be unreduced or reduced less than the first motion. The spring(s) 13 can generate a force on the second arrangement(s) which can facilitate a gradual constant tissue compression.

According to yet another exemplary embodiment of the present disclosure, the third arrangement(s) III can comprise a closure arrangement 10 which is structured to be moved toward and away from a tip portion of the first arrangement(s) I, and can include a contacting surface such as clamping surface 7b which is configured to increase and/or reduce the size of the opening and contact the anatomical structure(s). The first arrangement I can include a first handle structure, and the second arrangement(s) II can include a second handle structure which is configured to move toward the first handle structure. In addition, a tension-setting arrangement can be provided which couples the first and second arrangements to one another and can include a constant force spring 12 that is attached between the first handle structure and the closure arrangement such as closure member 9 of the second arrangement.

According to still another exemplary embodiment, when the anatomical structure is pressed by the closure arrangement such as closure member 10 of the third arrangement III, a motion of the closure arrangement can be reduced or stopped, and the second arrangement(s) II can slide over the closure arrangement of the third arrangement III in the first direction. Further, when the anatomical structure is pressed by the third arrangement(s), a tension of the spring 13 is increased which likely causes the second arrangement(s) II to at least reduce the first motion of the closure arrangement in the first direction and facilitate the second arrangement to slide over the closure arrangement of the third arrangement III.

In yet a further exemplary embodiment of the present disclosure, the first arrangement(s) I can include a first handle structure and an anascope structure non-releasably connected to one another. A second arrangement II can also be provided which can include at least one further spring arrangement such as spring 12 coupling the first and second arrangements I, II, to one another. The first arrangement(s) can include at least one handle portion, and the second arrangement(s) can comprise a first closure arrangement such as closure member 9 which is structured to be moved toward and away from a tip portion of the first arrangement I. The further spring arrangement(s) can be coupled to the handle portion(s) of the first handle structure and the first closure arrangement. The further spring arrangement(s) can facilitate a movement of the closure arrangement in a direction that is at least approximately opposite to the first direction. The first direction can be a distal direction.

According to yet a further exemplary embodiment of the present disclosure, the second arrangement(s) can include therein or thereon at least one electrode provided at or near the contacting surface. The electrode can be powered by an electrical power source. Such electrode(s) can be at least partially embedded within the first arrangement(s). The electrode(s)

can be configured to irradiate at least one area of the anatomical structure(s) when the anatomical structure is constricted in the opening by the second arrangement(s). Further, the second arrangement(s) can include therein or thereon at least one illumination arrangement which provides light to the anatomical structure(s).

These and other objects, features and advantages of the exemplary embodiment of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying figures showing illustrative embodiments of the present disclosure, in which:

FIG. 5A is a side view of a third part (component) of the device of FIG. 1;

FIG. 5B is a top view of the third part shown in FIG. 5A;

FIG. 5C is a right side perspective view of the third part shown in FIG. 5A;

FIG. 5D is a left side perspective view of the third part shown in FIG. 5A;

Figure 1:
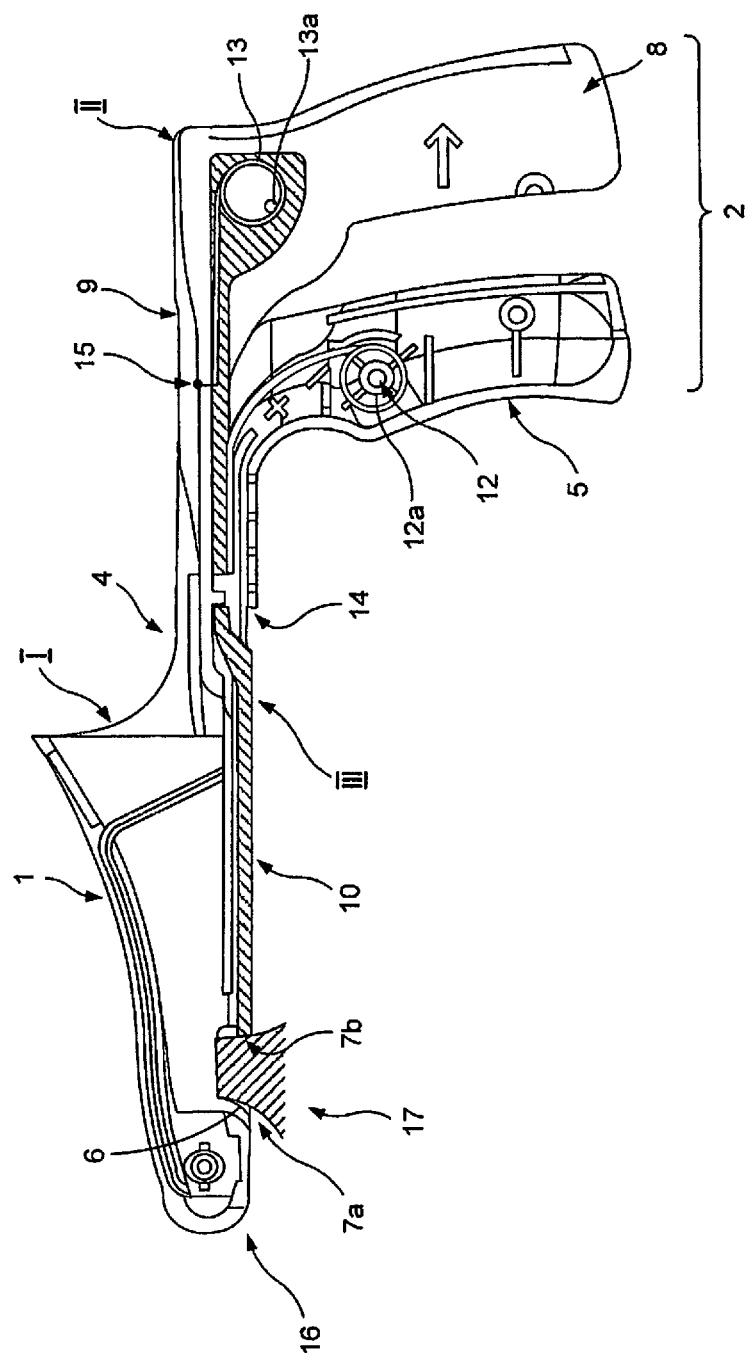
FIG. 1 is a side cross-sectional view of an exemplary embodiment of a device according to the present disclosure in an open position.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described exemplary embodiments without departing from the true scope and spirit of the subject disclosure as defined by the appended claims.

DETAILED DESCRIPTION OF EXEMPLARY EMBODIMENTS

FIGS. 1-6B show various components of an exemplary embodiment of a device according to the present disclosure. As shown in these drawings, the exemplary device has three primary parts, e.g., a first part or component (or member) I, a second part or component (or member) II and a third part or component (or member) III. The first part I (as shown in, e.g., FIGS. 1-3D) comprises a hollow portion 1 which includes a tapered end or insertion tip 16 which is structured or configured for insertion into or propagation through a bodily lumen or another anatomical structure, a first handle grip 5 (which is proximal (closer to the user) with respect to the tip 16) and a connecting section 4. The second part II (as shown in, e.g., FIGS. 1, 2, 2A, 2B and 4A-4D) comprises a second handle grip 8 (which is proximal with respect to the tip 16) and a first closure member 9, which can be non-releasibly connected. The third part III (as shown in, e.g., FIGS. 1, 2, 2A, 2B and 5A-5D) comprises a second closure member 10. The exemplary device provides a handle 2 (FIG. 1) which comprises the first handle grip 5 of the first part I and the second handle grip 8 of the second part II.

Figure 3A:
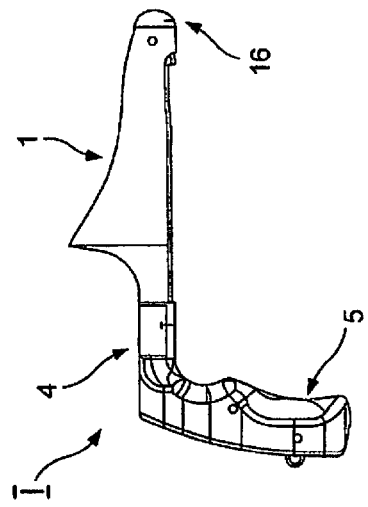
FIG. 3A is a left side cross-sectional view of a first part (component) of the device of FIGS. 1 and 2.
Figure 3B:
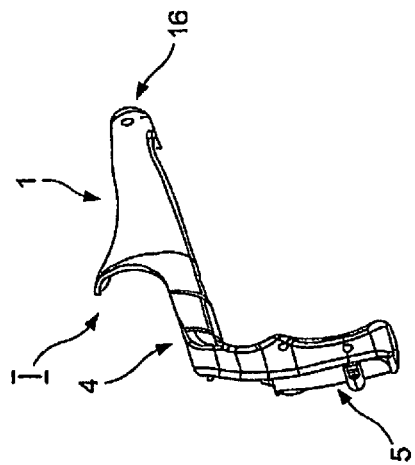
FIG. 3B is a right side cross-sectional view of the first part shown in FIG. 3A.
Figure 3C:
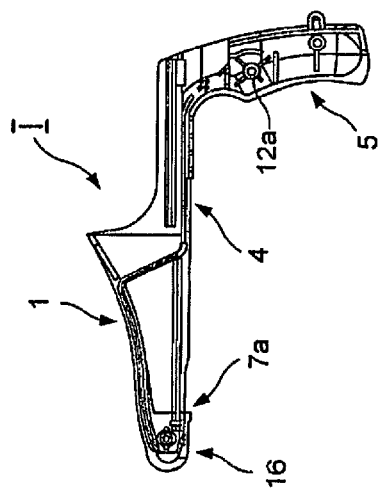
FIG. 3C is a right side perspective view of the first part shown in FIG. 3A.
Figure 3D:
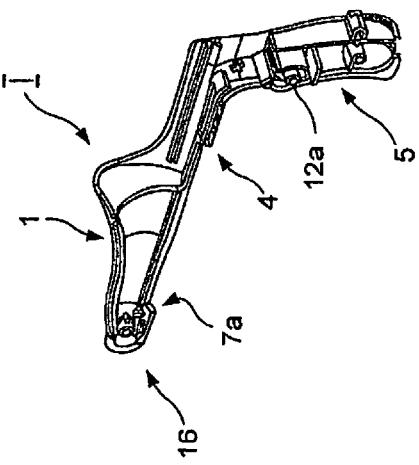
FIG. 3D is a left side perspective view of the first part shown in FIG. 3A.
Figure 4C:
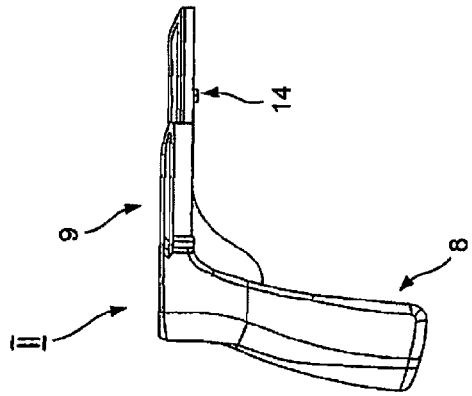
FIG. 4C is a right side view of the second part shown in FIG. 4A.
Figure 4B:
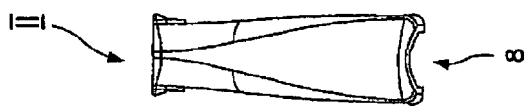
FIG. 4B is a rear view of the second part shown in FIG. 4A.
Figure 4D:
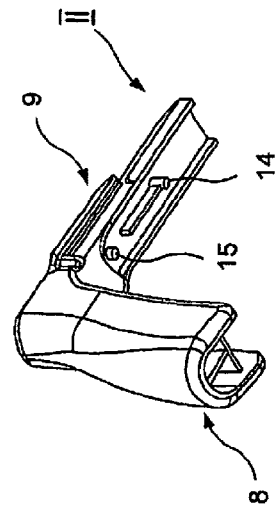
FIG. 4D is a perspective view of the second part shown in FIG. 4A.
Figure 4A:
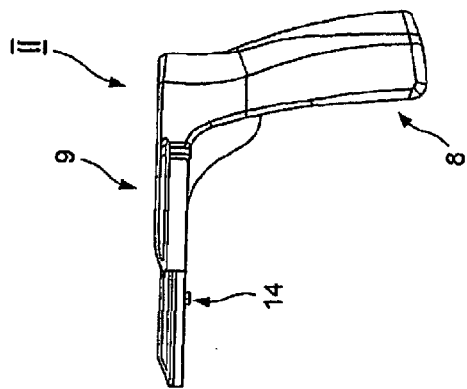
FIG. 4A is a right side view of a second part (component) of the device of FIG. 1.

Referring to FIGS. 1, 2, 2A, 2B, 6A and 6B, the exemplary device has a first spring 12 and a second spring 13, whereas the first spring 12 can be provided closer to the tip 16 than the second spring 13, and both of which can have two or more fixation points. Thus, the second spring 13 can be provided more proximal than the first spring 12. The first spring 12 can include (i) a first fixation point 12a provided at or on the first handle grip 5 of the first part I (as also shown in FIGS. 3A and 3C) and (ii) a second fixation point 14 (as also shown in FIGS. 2B, 4A, 4C and 4D) located on and below a surface of the first closure member 9 of the second part II. The second spring 13 also has (i) a first fixation point 13a located on or at the second closure member 10 of third part III (as also shown in FIGS. 5B and 5C), and (ii) a second fixation point 15 located on and below the surface of the first closure member 9 of second part II (as also shown in FIG. 4D).

Figure 6A:
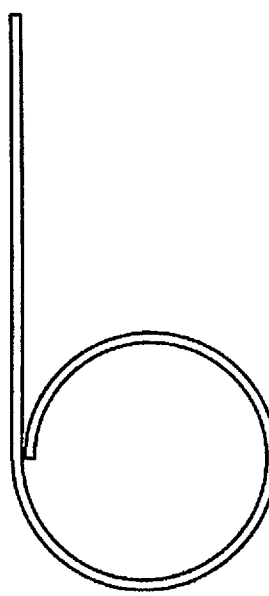
FIG. 6A is a lateral side view of a spring used in the device of FIG. 1.
Figure 6B:
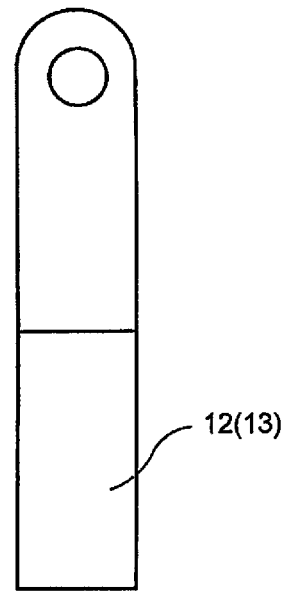
FIG. 6B is a front view of the spring illustrated in FIG. 6A.

When the exemplary device is assembled, the second spring 13 is provided or positioned just below a particular surface 20 of the second closure member 10, while also being coupled to the first fixation point 13a thereof. Any of the fixation points 12a, 13a, 14 and/or 15 can be metal and/or plastic knob(s) or other members to which the respective first and second springs 12, 13 can be attached, clipped unto and/or adhered to, e.g., possibly with glue, clips, etc. The exemplary details of the first and second springs 12, 13 are illustrated in FIGS. 6A and 6B. However, it should be understood that other shapes and/or or sizes of the springs are conceivable and are within the scope of the exemplary embodiments of the present disclosure.

FIGS. 1, 2, 2A and 2B show that the first spring 12 couples the first part I and the second part II to one another. These drawings also illustrate that the second spring 13 couples the first and second closure members 9, 10 of respective parts II and III to one another, which are slidably engaged with each other.

Figure 2:
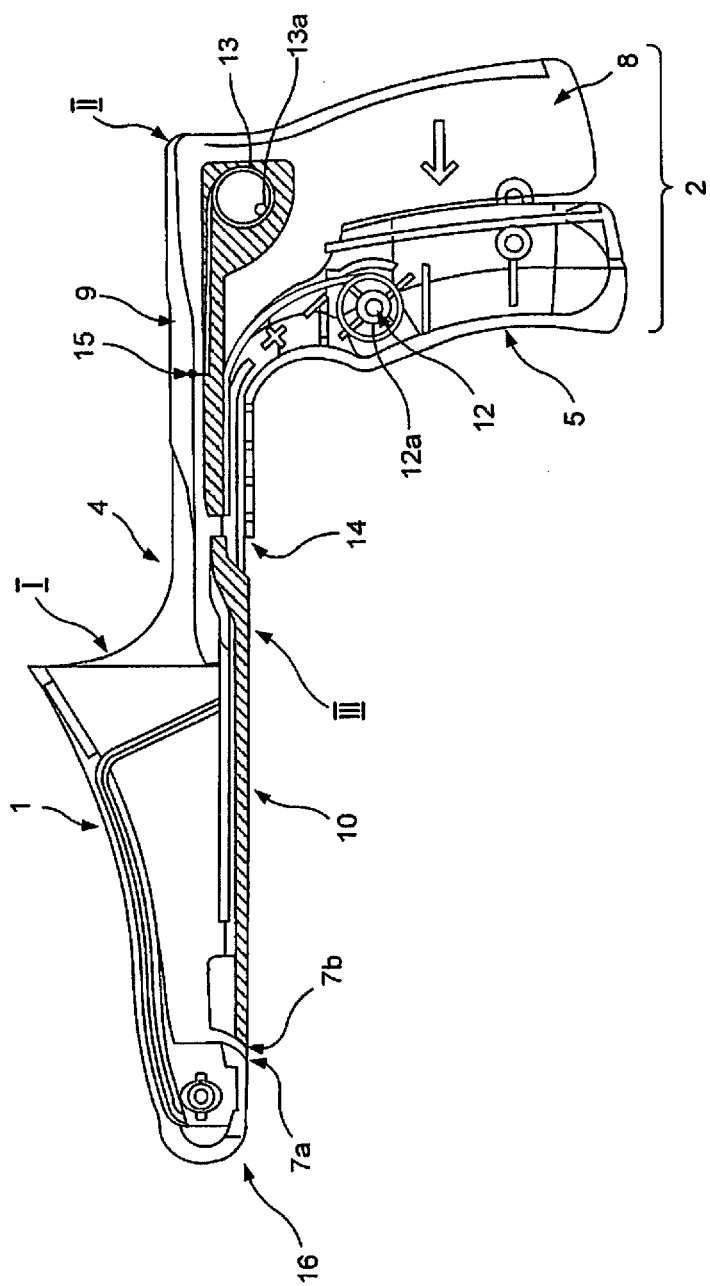
FIG. 2 is a side cross-sectional view of the device of FIG. 1 in a closed position.

As shown in FIGS. 1 and 2, the exemplary device includes a window 6 which is enclosed between and formed by at least two opposing clamping surfaces, e.g., a first opposing clamping surface 7a (which is part of the hollow portion 1 of the first part I), and a second opposing clamping surface 7b (which is part of the second closure member 10 of the third part III and provided on the edge thereof). The second clamping surface 7b is moved toward the first clamping surface 7a by moving the third part III toward the first clamping surface 7a to close or reduce the size of the window 6 and away from such first clamping surface 7a to open or increase the size of the window 6. Such movement of the third part III can be actuated by squeezing and/or releasing the handle 2 of the exemplary device.

For example, according to one exemplary embodiment of the present disclosure, when the second handle grip 8 is moved toward the first handle grip 5 by squeezing (see arrow of FIG. 2), during such exemplary squeezing motion by the operator's hand, the window 6 size is reduced, by, e.g., being closed until it meets an obstacle, such as, for example, a protruding tissue 17 (as shown in FIG. 1). In addition, the window 6 is intended to be closed when the first and second opposing clamping surfaces 7a, 7b meet each other (as shown in FIG. 2). Thus, the window 6 becomes bigger when the second closure member 10 moves away from the first opposing clamping surface 7a of the first part I, and smaller when the second closure member 10 moves towards the first opposing clamping surface 7a of the first part I.

Figure 2A:
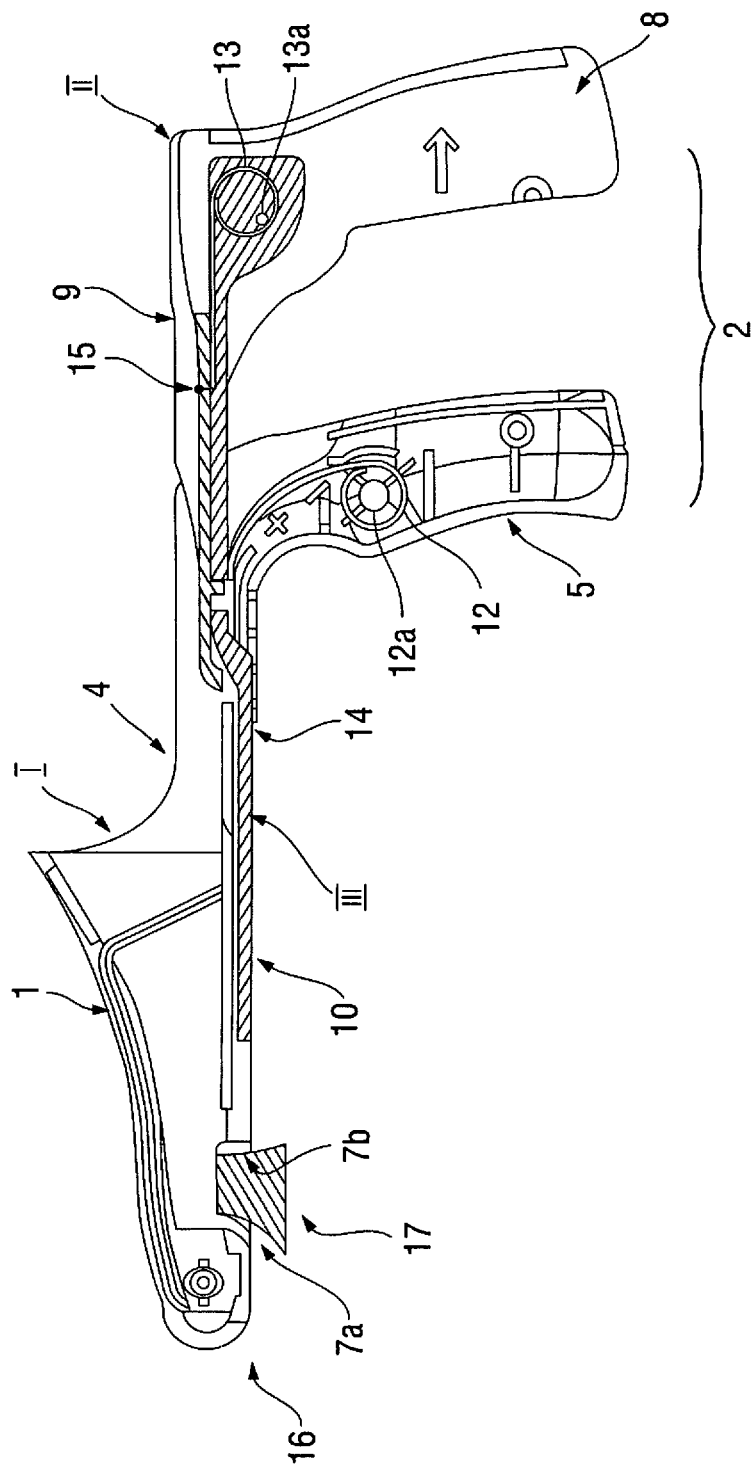
FIG. 2A is a side cross-sectional view of the device of FIG. 1 in a fully open position.
Figure 2B:
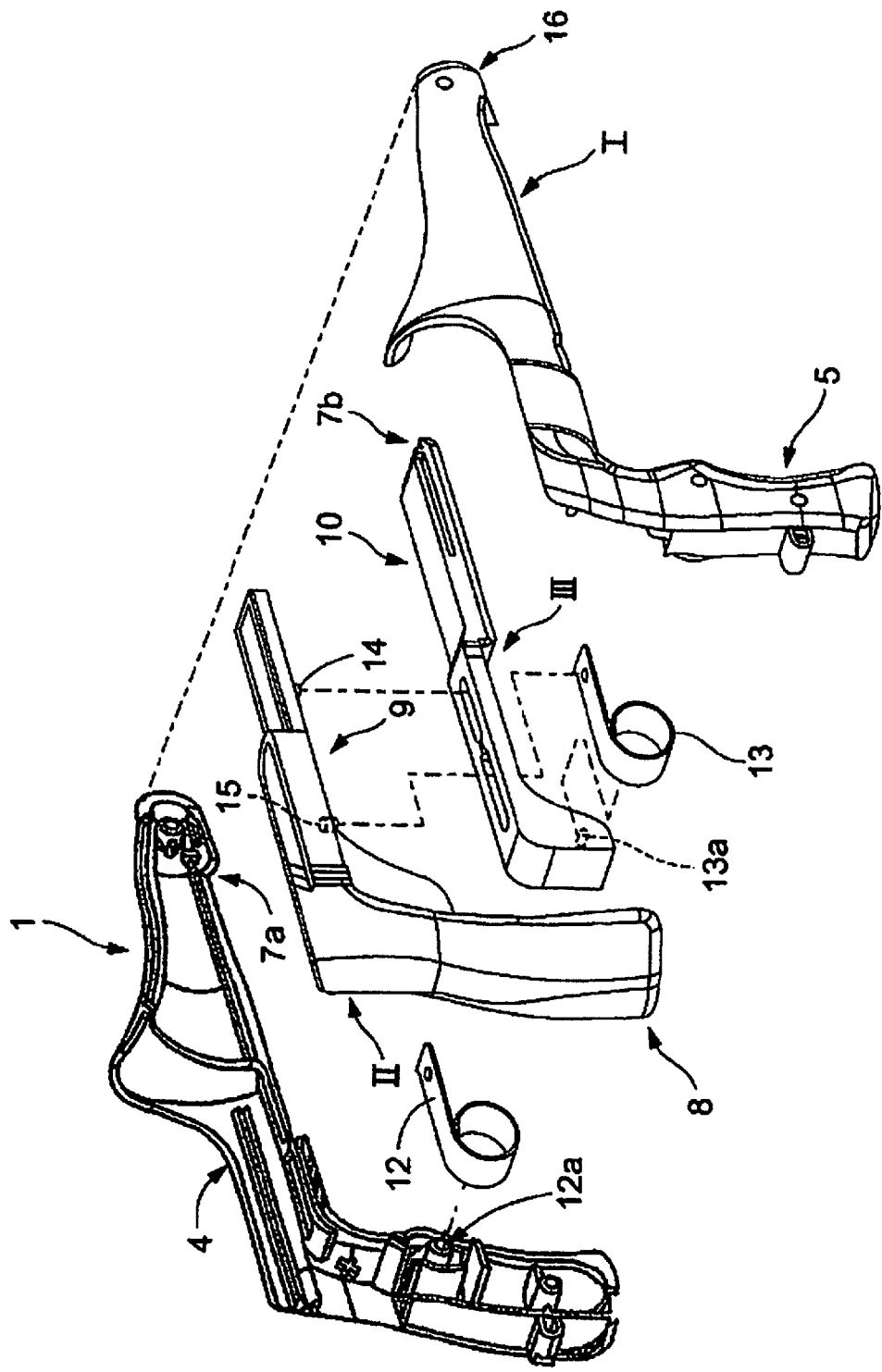
FIG. 2B is an exploded view of the device of FIG. 1.

In an exemplary operation, when the second handle grip 8 of the second part II. is moved toward the first handle grip 5 of the first part I (see FIG. 2), for example, during a squeezing motion by the hand of the operator, the second part II pulls on the second spring 13. This is because the second spring 13 is connected at one end thereof to the second part II via the second fixation point 15 (as shown in FIGS. 2A, 2B and 4D) which is located on and below a surface of the first closure member 9 of the second part II. The strength of the second spring 13 is selected or configured so as to facilitate the second main part II to pull the second closure member 10 of the third part III in the same direction as the direction of propagation of the first closure member 9. Indeed, during the exemplary operation, the second closure member 10 of the third part III is moved by the first closure member 9 of the second part II forward toward the first clamping surface 7a by pulling (e.g., likely without significant stretching) the second spring 13, provided that the second closure member 10 does not meet the obstacle in the window 6. Indeed, such pulling motion is effectuated since another end of the second spring 13 is connected to the first fixation point 13a located on or at the second closure member 10 and below the particular surface 20 thereof (as also shown in FIGS. 5B and 5C). Thus, the second spring 13 acts as a spring coupling arrangement between the second part II and the third part III.

Figure 2C:
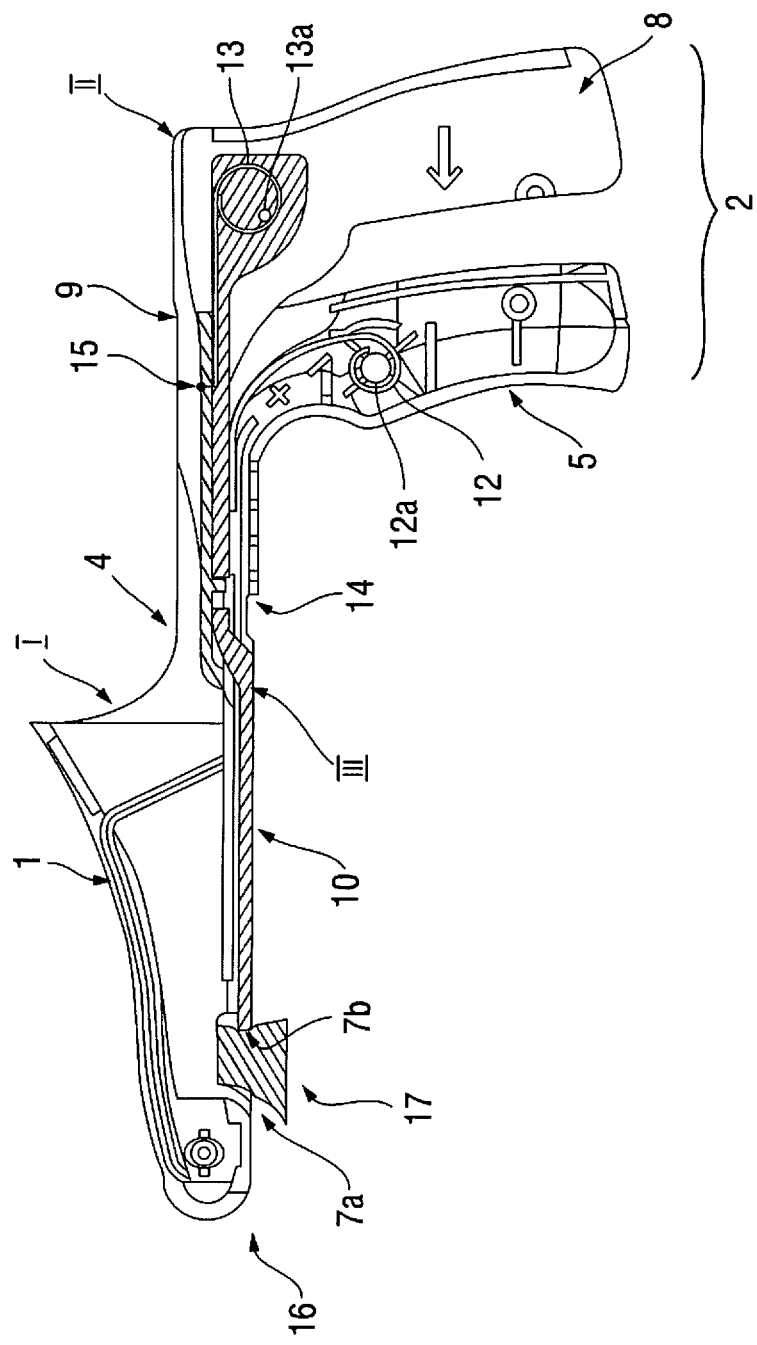
FIG. 2C is a side cross-sectional view of the device of FIG. 1 in a partially closed position wherein the tissue is compressed by the second closure member.
Figure 2D:
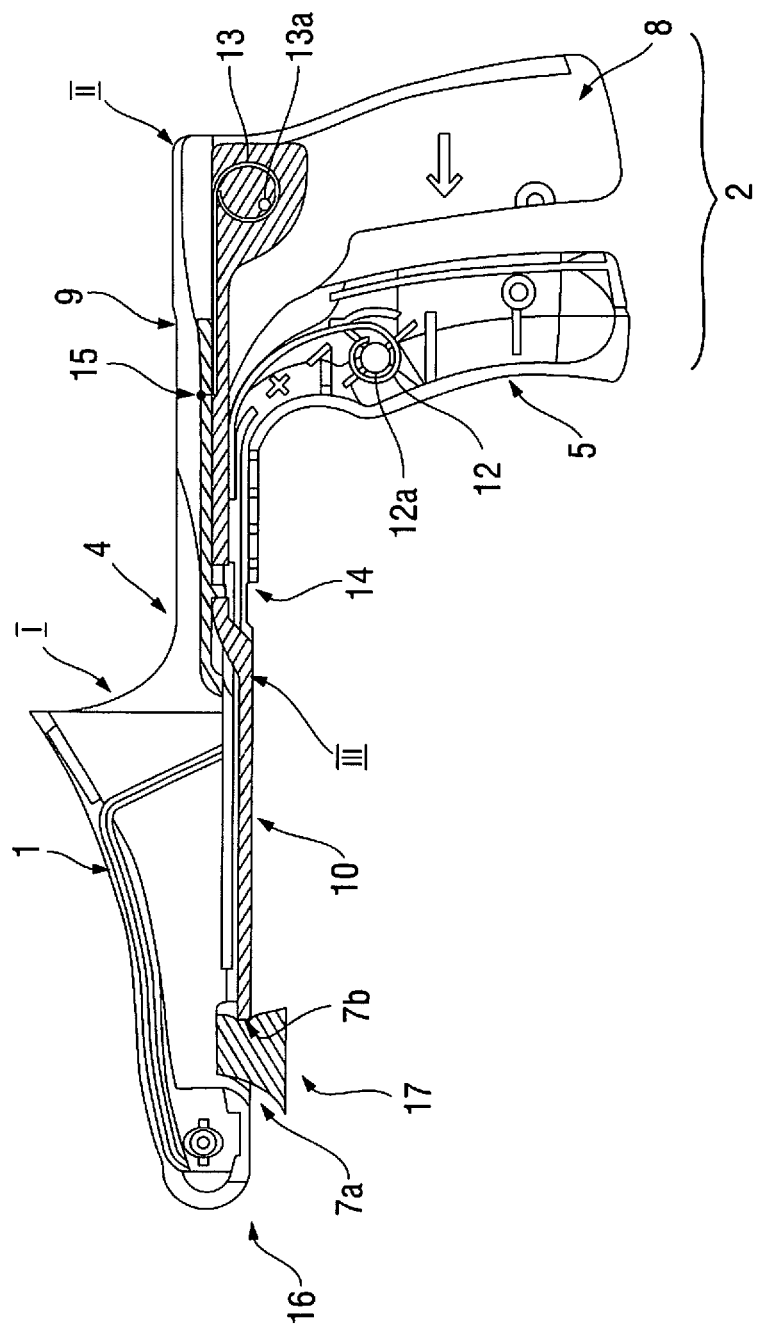
FIG. 2d is a side cross-sectional view similar to FIG. 2c showing movement of the first closure member with respect to the second closure member and tensioning of the spring.

As shown in FIG. 1, if the second closure member 10 of the third part III meets the obstacle in the window 6 (e.g., the protruding tissue), the forward motion of the second closure member 10 in the same direction as that of the second part II stops completely or for the most part as shown in FIG. 2C. At the same time, the second part II of the exemplary device continues to move forward in the same direction, and also (simultaneously) causes the second spring 13 to stretch as shown in FIG. 2D. As a result, the first closure member 9 of second part II slides over the second closure member 10 of the third part III towards the first clamping surface 7a or the end or tip 16, without further affecting the forward movement of the second closure member 10 of the third part III and absent any further significant compression of the tissue situated within the window 6 (see FIG. 2D).

This exemplary effect is caused by the fact that when the second opposing clamping surface 7b of the second closure member 10 of the third part III contacts and attempts to press on the tissue provided within the window 6, this negative pressure causes the second spring 13 to stretch. In this manner, while the second closure member 10 of the third part III is prevented from moving forward by the tissue, a tension is continued on the second spring 13, allowing the first closure member 9 of the second part II to continue its forward motion toward the tip 16. Such tension on the second spring 13 facilitates an approximately constant compression on the tissue. Indeed, as a result, a constant tissue compression (e.g., on the tissue or on any other object) can be accomplished in the window 6. Such constant tension or compression can be largely separate from or independent of the force exerted by the operator on the handle 2, for example, the compression of the tissue can be mainly dependent upon various properties of the second spring 13, the connections thereof to the second and third parts II, III, and the properties of the compressed tissue 17 in the window 6.

In addition, according to another exemplary embodiment of the present disclosure, the first spring 12 can be useful in facilitating the operation of the exemplary device. For example, when the second handle grip 8 of part II is moved toward the first handle grip 5 of part I (see arrow of FIG. 2), e.g., during the squeezing motion by the hand of the operator, the second part II is simultaneously pulled on and stretches the first spring 12 (as shown in FIG. 2). This is because one end of the first spring 12 is coupled to the second fixation point 14 (as shown in FIGS. 2B, 4A, 4C and 4D) located on and below the surface of the first closure member 9 of the second part II, and the other end of the first spring 12 is coupled to the first fixation point 12a provided at or on the first handle grip 5 of the first part I (as shown in FIGS. 3A and 3C). In this manner, the first spring 12 is stretched by the forward movement of the first closure member 9 of the second part II toward the first clamping surface 7a or the end or tip 16 of the first part I, while the first part I is stationary with respect to the tip 16.

During the exemplary operation, and referring to FIGS. 1 and 2A, when the squeezed handle 2 is released, the first spring 12 has the tension to cause itself to return to its original (e.g., non-stretched or less-stretch) configuration, thereby pulling on the first closure member 9 of the second part II until the second part II returns proximally to its non-deployed (e.g., open or original) position. Again, this is caused by the first spring 12 being attached to a stationary first part I via the first fixation point 12a, and pulling the first closure member 9 of the second part II back to its original position due to the first spring 12 being connected to the second fixation point 14 of the first closure member 9. In addition, as the second part II is in the process of returning to its non-deployed position (shown in FIG. 2A) with the assistance of the first spring 12, the second part II also pulls on and effectuates further tension of the second spring 13, which pulls back the second closure member 10 due to its coupling to the first fixation point 13a thereof until the second closure member 10 returns to its non-deployed position. When the second closure member 10 moves back to such position, the window 6 becomes enlarged, e.g., until it is fully open (as shown in FIG. 2A).

Figure 1A:
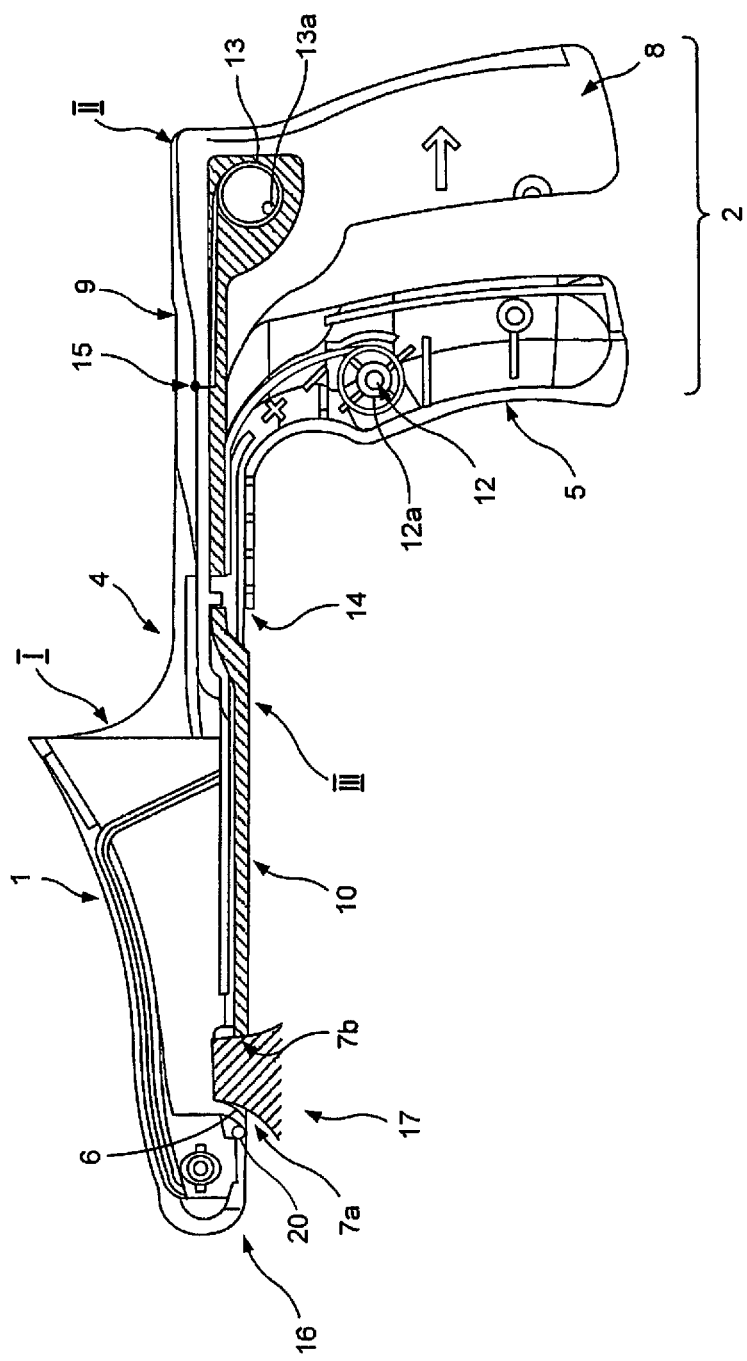
FIG. 1A is a side cross-sectional view of an alternate embodiment of the device of the present disclosure in an open position.
Figure 1B:
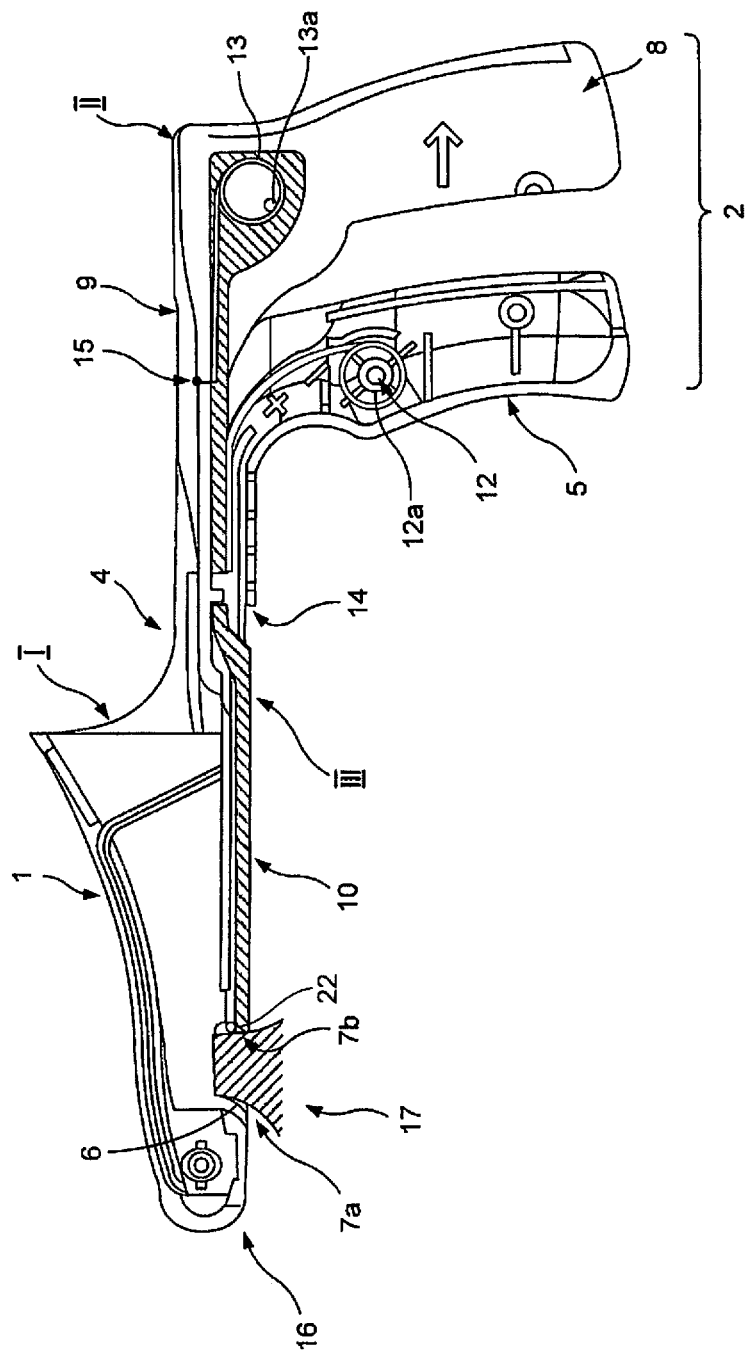
FIG. 1B is a side cross-sectional view of another alternate embodiment of the device of the present disclosure shown in an open position.
Figure 1C:
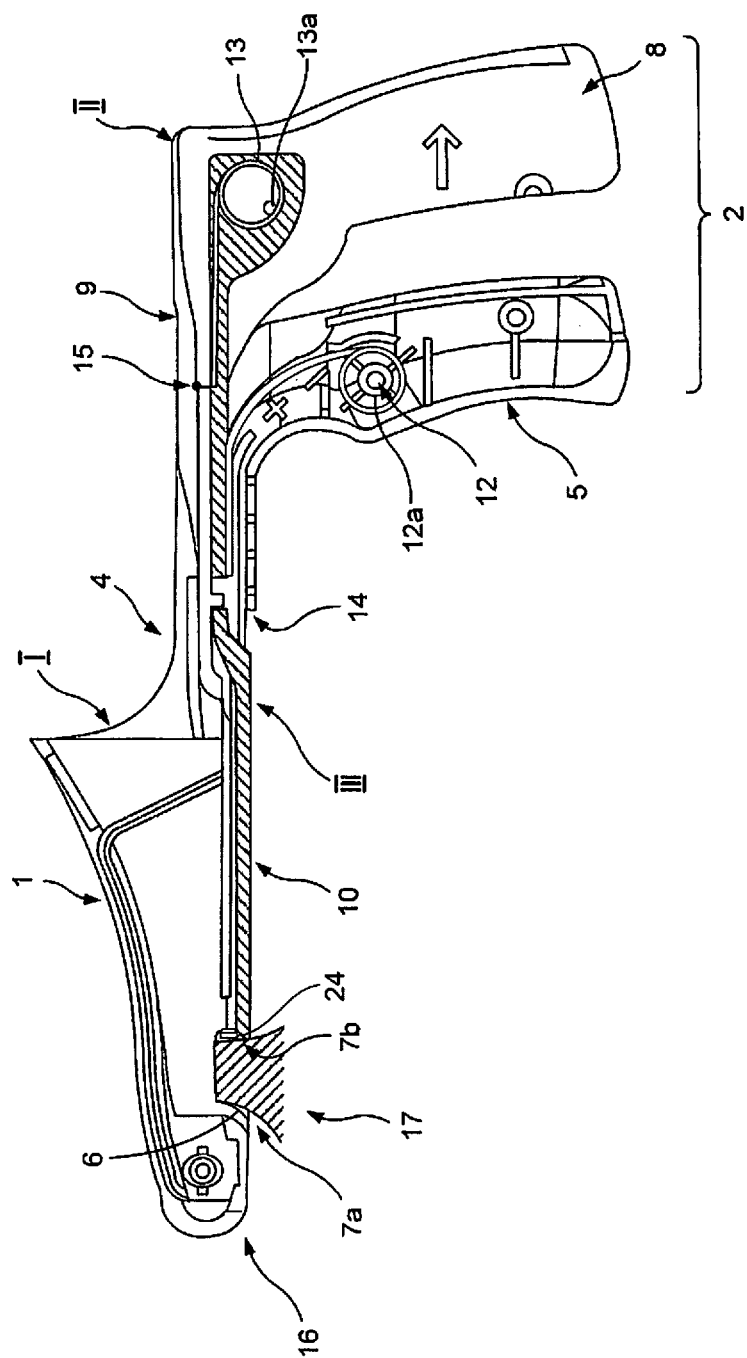
FIG. 1C is a side cross-sectional view of another alternate embodiment of the device of the present disclosure shown in an open position.

FIGS. 1A and 1B illustrate an electrode provided at or near the contacting surface as referenced above. The electrode 20 in FIG. 1A is shown embedded in the first part I. In the alternate embodiment of FIG. 1B, the electrode 22 is provided on second part II near the contacting surface of the clamping surface. FIG. 1C illustrates an illumination arrangement 24 on the second part II to provide light to the anatomical structure.

It will further be appreciated by those having ordinary skill in the art that, in general, terms used herein, and especially in the appended claims, are generally intended as open. In addition, to the extent that the prior art knowledge has not been explicitly incorporated by reference herein above, it is explicitly being incorporated herein in its entirety. All publications referenced above are incorporated herein by reference in their entireties. In the event of a conflict between the teachings of the application and those of the incorporated documents, the teachings of the application shall control. Various exemplary embodiments described herein can be used together, in combination and/or separately from one another in accordance with further exemplary embodiments of the present disclosure

What is claimed is:

1. An apparatus for effecting at least one anatomical structure of a body, comprising:
    at least one first arrangement which is structured to be at least partially inserted into the body and including an opening;
    at least one second arrangement operatively connected to the first arrangement;
    at least one third arrangement which is coupled to the at least one second arrangement, the at least one third arrangement movable to at least one of increase or decrease a size of the opening by a motion thereof in a first direction; and
    a tension-setting arrangement coupling the second and third arrangements to one another to effect movement;
    the second arrangement movable parallel to the first direction,
    wherein, during use of the apparatus to treat tissue when the at least one anatomical structure is provided in the opening and is pressed on by movement of the at least one third arrangement to decrease the size of the opening, a first motion of the at least one third arrangement toward the at least one anatomical structure in the first direction is at least one of reduced or terminated while a second subsequent motion of the at least one second arrangement at least one of (i) remains at least the same, or (ii) is reduced to a lesser extent than that of the first motion, the second arrangement remaining coupled to the third arrangement during the subsequent second motion, and the tension-setting arrangement maintaining the coupling of the second and third arrangements during the subsequent second motion.

2. The apparatus according to claim 1, wherein the tension-setting arrangement includes at least one spring which generates a force on the at least one third arrangement which facilitates a gradual constant tissue compression.

3. The apparatus according to claim 1, wherein the at least one third arrangement comprises a closure arrangement having a clamping surface which is moved toward and away from a tip portion of the at least one first arrangement when the third arrangement is moved, the clamping surface includes a contacting surface which is configured to contact the at least one anatomical structure.

4. The apparatus according to claim 3, wherein the at least one first arrangement includes a first handle structure, and wherein the at least one second arrangement includes a second handle structure which is configured to move toward the first handle structure.

5. The apparatus according to claim 4, further comprising a tension-setting arrangement which couples the first and second arrangements to one another and includes at least one spring, and wherein the at least one spring is a constant force spring that is attached between the first handle structure and a closure arrangement of the second arrangement.

6. The apparatus according to claim 3, wherein, when the at least one anatomical structure is pressed by the closure arrangement by actuation of a handle and the motion of the closure arrangement of the at least one third arrangement is at least one of reduced or stopped, continued actuation of the handle causes the at least one second arrangement to slide over the closure arrangement of the third arrangement in the first direction.

7. The apparatus according to claim 6, wherein the tension-setting arrangement which couples the second and third arrangements to one another includes at least one spring, wherein, when the at least one anatomical structure is pressed by the at least one third arrangement, a tension of the at least one spring is increased which causes the at least one third arrangement to at least reduce the first motion of the closure arrangement in the first direction and facilitates the at least one second arrangement to slide over the closure arrangement.

8. The apparatus according to claim 3, wherein the at least one second arrangement includes therein or thereon at least one electrode provided at or near contacting surface, the at least one electrode being powered by an electrical power source.

9. The apparatus according to claim 8, wherein the at least one electrode is configured to irradiate at least one area of the at least one anatomical structure when the at least one anatomical structure is constricted in the opening by the at least one third arrangement.

10. The apparatus according to claim 8, wherein the at least one second arrangement includes therein or thereon at least one illumination arrangement which provides light to the at least one anatomical structure.

11. The apparatus according to claim 3, further comprising at least one electrode, wherein the at least one electrode is at least partially embedded within the at least one first arrangement.

12. The apparatus according to claim 1, wherein the at least one first arrangement includes a first handle structure and an anascope structure non-releasably connected to one another.

13. The apparatus according to claim 1, further comprising at least coupling the first and second arrangements to one another by a spring.

14. The apparatus according to claim 13,
    wherein the at least one first arrangement includes at least one handle portion, and the at least one third arrangement comprises a closure arrangement which is structured to be moved toward and away from a tip portion of the at least one first arrangement, and
    wherein the spring is coupled to the at least one handle portion and the second arrangement.

15. The apparatus according to claim 14, wherein the spring facilitates a movement of the closure arrangement in a direction that is opposite to the first direction.

* * * * *